United States Patent [19]

Toyoshima et al.

[11] 4,278,666

[45] Jul. 14, 1981

[54] NOVEL ORGANOSILICON COMPOUNDS AND ANTI-TRANSPLANTED TUMOR AGENTS CONTAINING THE SAME

[75] Inventors: Shigeshi Toyoshima, Funabashi; Ryuichi Sato, Gunma; Koichi Ito, Higashi-kurume; Toshio Shinohara, Annaka; Yasushi Yamamoto, Takasaki, all of Japan

[73] Assignee: Shin-Etsu Chemical Co., Ltd., Tokyo, Japan

[21] Appl. No.: 124,957

[22] Filed: Feb. 26, 1980

[30] Foreign Application Priority Data

Mar. 12, 1979 [JP] Japan ................................ 54-28456

[51] Int. Cl.$^3$ ...................... C07F 7/10; A61K 31/725; A01N 55/00; A61K 31/695
[52] U.S. Cl. ...................................... 424/184; 556/422
[58] Field of Search ......................... 556/422; 424/184

[56] References Cited

U.S. PATENT DOCUMENTS

| | | | |
|---|---|---|---|
| 3,592,795 | 7/1971 | Ashby | 556/422 X |
| 3,697,568 | 10/1972 | Boissieras et al. | 556/422 |
| 3,826,782 | 7/1974 | Lengnick | 556/422 X |
| 4,033,991 | 7/1977 | Shinohara et al. | 556/422 X |
| 4,126,630 | 11/1978 | Müller et al. | 556/422 X |

*Primary Examiner*—Paul F. Shaver

[57] ABSTRACT

The invention provides a novel class of organosilicon compounds and a method for the preparation thereof as well as an anti-tumor agent containing the compound having very remarkable anti-tumor activity but with very low toxicity. The inventive compound is a (trihydrocarbylsilylmethyloxyimino)alkane, which is a silicon-containing oxime compound hitherto not described in any prior art literatures, represented by the general formula $R^1{}_3Si-CH_2-O-N=Y$, $R^1$ is a substituted or unsubstituted monovalent hydrocarbon group having from 1 to 10 carbon atoms and Y is a divalent hydrocarbon group denoted by $=CR^2R^3$ or $=CR^4$, $R^2$ and $R^3$, which may be identical or different, having the same meaning as $R^1$ defined above and $R^4$ being an alkylene group to form a ring structure jointly with the carbon atom directly bonded to the nitrogen atom. Typical examples of the compounds are: 2-(trimethylsilylmethyloxyimino) butane, 2-(trimethylsilylmethyloxyimino)propane, 2-(dimethylphenylsilylmethyloxyimino) butane and trimethylsilylmethyloxyiminocyclohexane.

13 Claims, No Drawings

NOVEL ORGANOSILICON COMPOUNDS AND ANTI-TRANSPLANTED TUMOR AGENTS CONTAINING THE SAME

BACKGROUND OF THE INVENTION

The present invention relates to a novel class of organosilicon compounds and an anti-tumor agent containing the organosilicon compound as the therapeutically effective ingredient. More particularly, the invention relates to silicon-containing oxime compounds and an anti-tumor agent containing a therapeutically effective amount of the oxime compound.

There have been hitherto known various kinds of organosilicon compounds having anti-tumor activity. For example, silatolan compounds belong to one of the classes of such organosilicon compounds having anti-tumor activity although silatolan compounds are not widely used in the actual therapy because of the relatively strong toxicity of the compounds. Other classes of organosilicon compounds also suffer from similar problems and, accordingly, there has been a strong desire to obtain a novel class of organosilicon compounds effective as an anti-tumor agent with low or no toxicity.

SUMMARY OF THE INVENTION

The primary object of the present invention is to provide a novel anti-tumor agent comprising, as its therapeutically effective ingredient, an organosilicon compound having activity as an anti-tumor agent and yet having low or no toxicity. As used herein, the term 'anti-tumor' means 'anti transplanted tumor.'

Another object of the invention is to provide a novel organosilicon compound not described in any prior art literatures.

The novel organosilicon compound, which is the main ingredient contained in a therapeutically effective amount in the inventive anti-tumor agent, is a silicon-containing oxime compound named as a (thrihydrocarbylsilylmethyloxyimino) alkane and represented by the general formula $$R^1{}_3Si-CH_2-O-N=Y, \quad (I)$$

where $R^1$ is a substituted or unsubstituted monovalent hydrocarbon group having from 1 to 10 carbon atoms and Y is a divalent hydrocarbon group denoted by $=CR^2R^3$ or $=CR^4$, $R^2$ and $R^3$, which may be identical or different, having the same meaning as $R^1$ defined above and $R^4$ being a divalent hydrocarbon group, e.g. an alkylene group.

The anti-tumor agent containing the compound of the above general formula (I) in a therapeutically effective amount exhibits strong anti-tumor activity with extremely low toxicity.

DETAILED DESCRIPTION OF THE PREFERRED EMBODIMENTS

The silicon-containing oxime compound as the main ingredient of the inventive anti-tumor agent is represented by the above given general formula (I) and belongs to a novel class of organosilicon compounds hitherto not known or not described in any prior art literatures.

In the general formula (I), $R^1$ is a substituted or unsubstituted monovalent hydrocarbon group having from 1 to 10 carbon atoms as exemplified by alkyl groups such as methyl, ethyl, propyl and the like, alkenyl groups such as vinyl, allyl and the like, cycloalkyl groups such as cyclohexyl and the like, aryl groups such as phenyl and the like and aralkyl groups such as phenylethyl and the like as well as those groups derived from the above named hydrocarbon groups by the substitution of, for example, halogen atoms or other substituent atoms or groups for part or all of the hydrogen atoms in the hydrocarbon groups as exemplified by chloromethyl, 3,3,3-trifluoropropyl, 3-methoxypropyl, 3-thiomethoxypropyl, 2-, 3- or 4-chlorophenyl, 3, 4-dichlorophenyl, 2-, 3- or 4-methoxyphenyl and the like. Among the above named substituted or unsubstituted monovalent hydrocarbon groups, the most preferred are methyl, ethyl, vinyl and phenyl groups by the reason of easiness in the synthetic preparation. Three of the groups $R^1$ bonded to the same silicon atom may be identical with or different from each other.

The groups denoted by the symbols $R^2$ and $R^3$ are each a substituted or unsubstituted monovalent hydrocarbon group as $R^1$ defined above but, preferably, they are each a lower alkyl group having from 1 to 4 carbon atoms or a phenyl group. On the other hand, $R^4$ is a divalent hydrocarbon group, preferably, an alkylene group having from 3 to 6 carbon atoms so as to form a ring structure jointly with the carbon atom directly bonded to the nitrogen atom. The most preferred for $R^4$ is pentene group $-(CH_2)_5-$  which forms a cyclohexane ring with the carbon atom bonded to the nitrogen atom.

Thus, several of the examples of the silicon-containing oxime compounds in conformity with the general formula (I) and the definitions of the symbols described above are: 2-(trimethylsilylmethyloxyimino)butane: 2-(trimethylsilylmethyloxyimino) propane, 2-(dimethylphenylsilylmethyloxyimino)butane; and trimethylsilylmethyloxyiminocyclohexane.

In the following, a method for the synthetic preparation of the inventive silicon-containing oxime compounds is described.

The starting materials of the synthetic procedure are a ketoxime compound represented by the general formula $$HO-N=Y, \quad (II)$$

where Y has the same meaning as defined above, and a chloromethyl-containing trihydrocarbylsilane represented by the general formula $$R^1{}_3Si-CH_2Cl, \quad (III)$$

where $R^1$ has the same meaning as defined above. The ketoxime compound of the general formula (II) is first reacted with metallic sodium in an inert organic solvent such as toluene to form a sodium salt of the ketoxime $NaO-N=Y$, which is further reacted with the chloromethyl-containing trihydrocarbylsilane of the general formula (III) in a polar organic solvent such as N,N-dimethylformamide with formation of sodium chloride as a byproduct.

The above mentioned ketoxime compound is exemplified by methylethylketoxime, acetoxime, cyclohexanoneoxime, butanoxime and the like and the chloromethyl-containing trihydrocarbylsilane is exemplified by trimethylchloromethylsilane, dimethylphenylchloromethylsilane and the like.

Following are the examples to illustrate the synthetic preparation and identification of the inventive silicon-containing oxime compounds and the effectiveness of these novel compounds as the main ingredient of the inventive anti-tumor agents.

EXAMPLE 1

Preparation of 2-(trimethylsilylmethyloxyimino)butane

A fine dispersion of metallic sodium was obtained by adding 10.4 g (0.45 mole) of metallic sodium to 100 ml of toluene and heating the mixture under reflux to melt the sodium with vigorous agitation followed by cooling to room temperature.

To the above obtained dispersion of metallic sodium was added 34.8 g (0.4 mole) of methylethylketoxime and the reaction mixture was heated at 60° to 80° C. for about 180 minutes followed by removal of toluene under reduced pressure to give pasty sodium salt of methylethylketoxime. Then, this sodium salt of methylethylketoxime was dispersed in a mixture of 49.2 g (0.4 mole) of trimethylchloromethylsilane and 100 ml of N,N-dimethylformamide and heated at 70° to 80° C. for 3 hours with agitation. The reaction mixture after completion of the reaction was washed with water to remove sodium chloride formed as the by-product and N,N-dimethylformamide and the residue was extracted with diethyl ether followed by evaporation of the ether to give a crude product which was further distilled under reduced pressure to give 48.4 g of a liquid product boiling at 84° C. under 50 mmHg. This product is referred to as compound S-I hereinafter.

The results of elementary analysis, NMR analysis and infrared absorption spectroscopy undertaken with this compound S-I supported that the compound was 2-(trimethylsilylmethyloxyimino) butane $C_8H_{19}ONSi$. The above given yield was 70% of the theoretical value.

Results of elementary analysis:

|    | Found, % | Calculated, % |
|----|----------|---------------|
| C  | 55.3     | 55.5          |
| H  | 11.2     | 11.1          |
| Si | 16.3     | 16.2          |
| N  | 7.9      | 8.1           |

NMR spectroscopy:

| δ ($CCl_4$) | 0.05 (9H, s); 1.05 (3H, t, J = 7 Hz) |
|             | 1.75 (3H, s); 2.13 (2H, g); 3.76 (2H, s) |

Infrared absorption spectroscopy: (taken as neat): absorption bands appearing at 1242, 1025, 901 and 850 $cm^{-1}$

EXAMPLE 2

Preparation of 2-(trimethylsilylmethyloxyimino) propane

Sodium salt of acetoxime was prepared in a similar procedure of Example 1 with 11.5 g (0.5 mole) of metallic sodium and 36.5 g (0.5 mole) of acetoxime and the reaction of the above sodium salt and trimethylchloromethylsilane was carried out by adding 61.5 g (0.5 mole) of the silane and 100 ml of N, N-dimethylformamide to the sodium salt to give 58.0 g of a liquid product boiling at 77° C. under 75 mmHg. This product is referred to as compound S-II hereinafter.

The results of elementary analysis, NMR analysis and infrared absorption spectroscopy undertaken with this compound S-II supported that the compound was 2-(trimethylsilylmethyloxyimino)propane $C_7H_{17}ONSi$. The above given yield was 73% of the theoretical value.

Results of elementary analysis:

|    | Found, % | Calculated, % |
|----|----------|---------------|
| C  | 52.6     | 52.8          |
| H  | 10.8     | 10.8          |
| Si | 17.9     | 17.6          |
| N  | 8.7      | 8.8           |

NMR spectroscopy: ($C_6D_6$) 0.06 (9H, s); 2.76 (6H, s); 2.83 (2H, s)

Infrared absorption spectroscopy: (taken as neat): absorption bands appearing at 1248, 1024, 910 and 858 $cm^{-1}$

EXAMPLE 3

Preparation of trimethylsilylmethyloxyiminoclohexane

Sodium salt of cyclohexanoneoxime was prepared in a similar procedure to Example 1 by the reaction of 11.5 g (0.5 mole) of metallic sodium and 56.5 g (0.5 mole) of cyclohexanoneoxime and the reaction of the above sodium salt and trimethylchloromethylsilane was carried out by adding 61.5 g (0.5 mole) of the silane and 100 ml of N,N-dimethylformamide to the sodium salt to give 66.7 g of a liquid product boiling at 75° C. under 5 mmHg. This product is referred to as compound S-III hereinafter.

The results of elementary analysis, NMR analysis and infrared absorption spectroscopy undertaken with this compound S-III supported that the compound was trimethylsilylmethyloxyiminocyclohexane $C_{10}H_{21}ONSi$. The above given yield of the compound was 67% of the theoretical value.

Results of elementary analysis:

|    | Found, % | Calculated, % |
|----|----------|---------------|
| C  | 60.3     | 60.2          |
| H  | 10.4     | 10.6          |
| Si | 14.2     | 14.1          |
| N  | 7.2      | 7.0           |

EXAMPLE 4

Preparation of 2-(dimethylphenylsilylmethyloxyimino) butane

Sodium salt of methylethylketoxime was prepared in a similar procedure to Example 1 by the reaction of 11.5 g (0.5 mole) of metallic sodium and 43.5 g (0.5 mole) of methylethylketoxime and the reaction of the above sodium salt and dimethylphenylchloromethylsilane was carried out by adding 93 g (0.5 mole) of the silane and 100 ml of N,N-dimethylformamide to the sodium salt to give 83.4 g of a liquid product boiling at 113° to 118° C. under 7 mmHg. This product is referred to as compound S-IV hereinafter.

The results of elementary analysis, NMR analysis and infrared absorption spectroscopy undertaken with this compound S-IV supported that the compound was 2-(dimethylphenylsilylmethyloxyimino)butane $C_{13}H_{21}ONSi$. The above given yield of the compound was 71% of the theoretical value.

Results of elementary analysis:

|   | Found, % | Calculated, % |
|---|---|---|
| C | 66.1 | 66.3 |
| H | 8.8 | 9.0 |
| Si | 12.1 | 11.9 |
| N | 5.9 | 6.0 |

EXAMPLE 5

Each of 36 BDF$_1$ female mice belonging to 6 groups, one being the control group and the other five being the test groups each composed of 6 mice, was inoculated with $5.7 \times 10^5$ cells of B-16 melanoma subcutaneously. The mice belonging to the control group were bred continuously as such. Each of the six mice belonging to either one of the five test groups was administrated by intraperitoneal injection with 300 mg a time per day of either one of the inventive compounds S-I to S-IV prepared in Example 1 to 4 above or 13.8 mg a time per day of 5-fluorouracil, each of the compounds being administrated as suspended in a sugar ester, beginning on the second day of inoculation to the sixth day. The amount of administration of 5-fluorouracil was decreased because the toxicity of this compound was so strong that the value of the LD$_{50}$ of this compound was one twentieth or smaller of the values of the inventive compounds S-I to S-IV.

After 14 days from the transplantation of the tumor cells, the mice were killed and the average weight of the tumor cells was determined for each of the groups. The values of the average tumor weights were utilized for the calculation of the inhibiting efficiency by the following equation to give the results set out in Table 1 below.

TABLE 1

$$\text{inhibiting efficiency} = \frac{\text{Average weight of tumor in the control group} - \text{Average weight of tumor in the test group}}{\text{Average weight of tumor in the control group}}$$

| Anti-tumor agent | Inhibiting efficiency, % |
|---|---|
| S-I | 76.4 |
| S-II | 73.2 |
| S-III | 71.3 |
| S-IV | 73.0 |
| 5-fluorouracil | 21.6 |

EXAMPLE 6

Each of 36 BDF$_1$ female mice belonging to 6 groups, one being the control group and the other five being the test groups each composed of 6 mice, was inoculated subcutaneously with $5 \times 10^5$ cells of Lewis cancer cells. The mice belonging to the control group were bred continuously as such. Each of the 6 mice belonging to either one of the five test groups was administrated by intraperitoneal injection with 300 mg a time per day of either one of the inventive compounds S-I to S-IV or 13.8 mg a time per day of 5-fluorouracil, each of the compounds being administrated as suspended in a sugar ester, beginning on the second day of inoculation to the sixth day.

After 14 days from the transplantation of the cancer cells, the mice were killed and the average weight of the cancer cells was determined for each of the groups. The values of the average cancer weight were utilized for the calculation of the inhibiting efficiency in the same manner as in Example 5 to give the results set out in Table 2 below.

TABLE 2

| Anti-tumor agent | Inhibiting efficiency, % |
|---|---|
| S-I | 63.9 |
| S-II | 62.5 |
| S-III | 60.4 |
| S-IV | 61.8 |
| 5-fluorouracil | 43.3 |

What is claimed is:

1. A (trihydrocarbylsilylmethyloxyimino)alkane represented by the general formula $$R^1{}_3Si-CH_2-O-N=Y,$$

where $R^1$ is a substituted or unsubstituted monovalent hydrocarbon group having from 1 to 10 carbon atoms and Y is a divalent hydrocarbon group denoted by $=CR^2R^3$ or $=CR^4$, $R^2$ and $R^3$, which may be identical or different, having the same meaning as $R^1$ defined above and $R^4$ being a divalent hydrocarbon group which forms a ring structure jointly with the carbon atom bonded to the nitrogen atom.

2. The (trihydrocarbylsilylmethyloxyimino)alkane as claimed in claim 1 which is 2-(trimethylsilylmethyloxyimino)butane.

3. The (trihydrocarbylsilylmethyloxyimino)alkane as claimed in claim 1 which is 2-(trimethylsilylmethyloxyimino)propane.

4. The (trihydrocarbylsilylmethyloxyimino)alkane as claimed in claim 1 which is 2-(dimethylphenylsilylmethyloxyimino)butane.

5. The (trihydrocarbylsilylmethyloxyimino)alkane as claimed in claim 1 which is trimethylsilylmethyloxyiminocyclohexane.

6. A method for the preparation of a (trihydrocarbylsilylmethyloxyimino)alkane represented by the general formula $$R^1{}_3Si-CH_2-O-N=Y,$$

where $R^1$ is a substituted or unsubstituted monovalent hydrocarbon group having from 1 to 10 carbon atoms and Y is a divalent hydrocarbon group denoted by $=CR^2R^3$ or $=CR^4$, $R^2$ and $R^3$, which may be identical or different, having the same meaning as $R^1$ defined above and $R^4$ being a divalent hydrocarbon group which forms a ring structure jointly with the carbon atom bonded to the nitrogen atom, which comprises;

(a) reacting a ketoxime represented by the general formula $$HO-N=Y,$$

where Y has the same meaning as defined above, with metallic sodium to form a sodium salt of the ketoxime, and (b) reacting the sodium salt of the ketoxime with a trihydrocarbylchloromethylsilane represented by the general formula $$R^1{}_3Si-CH_2Cl,$$

where $R^1$ has the same meaning as defined above.

7. The method as claimed in claim 6 wherein the reaction of the sodium salt of the ketoxime with the trihydrocarbylchloromethylsilane is carried out in a polar organic solvent.

8. The method as claimed in claim 6 wherein the ketoxime is methylethylketoxime and the trihydrocarbylchloromethylsilane is trimethylchloromethylsilane.

9. The method as claimed in claim 6 wherein the ketoxime is acetoxime and the trihydrocarbylchloromethylsilane is trimethylchloromethylsilane.

10. The method as claimed in claim 6 wherein the ketoxime is methylethylketoxime and the trihydrocarbylchloromethylsilane is dimethylphenylchloromethylsilane.

11. The method as claimed in claim 6 wherein the ketoxime is cyclohexanoneoxime and the trihydrocarbylchloromethylsilane is trimethylchloromethylsilane.

12. An anti-transplanted tumor agent which comprises a (trihydrocarbylsilylmethyloxyimino)alkane represented by the general formula $$R^1{}_3Si-CH_2-O-N=Y,$$

where $R^1$ is a substituted or unsubstituted monovalent hydrocarbon group having from 1 to 10 carbon atoms and Y is a divalent hydrocarbon group denoted by $=CR^2R^3$ or $=CR^4$, $R^2$ and $R^3$, which may be identical or different, having the same meaning as $R^1$ above and $R^4$ being a divalent hydrocarbon group which forms a ring structure jointly with the carbon atom bonded to the nitrogen atom, in a therapeutically effective amount with a pharmaceutically acceptable carrier.

13. The anti-transplanted tumor agent as claimed in claim 12 wherein the (trihydrocarbylsilylmethyloxyimino)alkane is selected from the class consisting of 2-(trimethylsilylmethyloxyimino)butane, 2-(trimethylsilylmethyloxyimino)propane, 2-(dimethylphenylsilylmethyloxyimino)butane and trimethylsilylmethyloxyiminocyclohexane.

* * * * *